United States Patent [19]
Yokozawa et al.

[11] Patent Number: 5,847,222
[45] Date of Patent: Dec. 8, 1998

[54] OPTICALLY ACTIVE DIPHOSPHINE COMPOUND, METHOD FOR MAKING THE COMPOUND, TRANSITION METAL COMPLEX HAVING THE COMPOUND AS LIGAND AND METHOD FOR MAKING OPTICALLY ACTIVE SUBSTANCE BY USE OF THE COMPLEX

[75] Inventors: Tohru Yokozawa; Noboru Sayo; Kazuhiko Matsumura; Hidenori Kumobayashi, all of Hiratsuka, Japan

[73] Assignee: Takasago International Corporation, Kanagawa, Japan

[21] Appl. No.: 918,347

[22] Filed: Aug. 26, 1997

[30] Foreign Application Priority Data

Aug. 27, 1996 [JP] Japan .................................. 8-261112

[51] Int. Cl.$^6$ ...................................................... C07F 9/52
[52] U.S. Cl. ................................................. 568/16; 568/17
[58] Field of Search ........................................ 568/16, 17

[56] References Cited

U.S. PATENT DOCUMENTS

| | | | |
|---|---|---|---|
| 4,556,740 | 12/1985 | Hansen | 568/13 |
| 5,516,944 | 5/1996 | Broger | 568/13 |
| 5,621,128 | 4/1997 | Jendralla | 556/18 |

Primary Examiner—Gary Geist
Assistant Examiner—Jean F. Vollano
Attorney, Agent, or Firm—Kubovcik & Kubovcik

[57] ABSTRACT

The present invention provides a ligand for a novel catalyst superior in such characteristics as selectivity (chemoselectivity and enantioselectivity) and catalytic activity in asymmetric synthesis reactions and a ligand for a novel catalyst effective in an asymmetric hydrogenation reaction in particular. The ligand is an optically active diphosphine compound represented by the following formula:

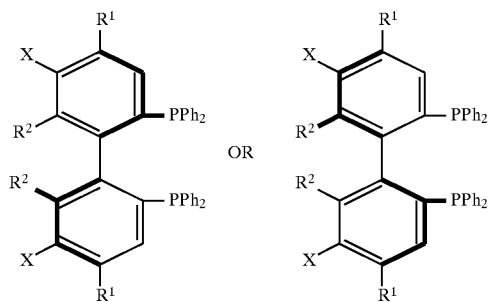

where Ph is a phenyl group, X is a chlorine or bromine atom, and $R^1$ and $R^2$ are each an alkyl group having 1 to 3 carbon atoms.

5 Claims, No Drawings

OPTICALLY ACTIVE DIPHOSPHINE COMPOUND, METHOD FOR MAKING THE COMPOUND, TRANSITION METAL COMPLEX HAVING THE COMPOUND AS LIGAND AND METHOD FOR MAKING OPTICALLY ACTIVE SUBSTANCE BY USE OF THE COMPLEX

BACKGROUND OF THE INVENTION

1. Field of the Invention

The present invention relates to a novel optically active phosphine compound, a method for making the same compound and a transition metal complex having the same compound as a ligand. The present invention also relates to a method for making an optically active substance by the asymmetric hydrogenation of acetol using the transition metal complex.

2. Description of Related Art

As asymmetric synthesis reactions, an asymmetric hydrogenation, an asymmetric isomerization, an asymmetric hydrosilylation and the like have hitherto been known. A transition metal complex is known to be effective as a catalyst in these reactions. In particular, a complex which comprises a transition metal such as ruthenium, rhodium, iridium or palladium coordinated with an optically active tertiary phosphine compound, has superior characteristics as a catalyst for the asymmetric synthesis reactions.

In order to further improve the catalytic performance, many phosphine compounds having various structures have been reported (see, for example, Introductory Chemistry 32, "Chemistry of Organometallic Complexes", pp.237–238, Ed. Organic Synthesis", Y. Noi, A wiley-Interscience Publication, 1996).

In particular, 2,2'-bis(diphenylphosphino)-1,1'-binaphthyl (hereinafter referred to as BINAP) is one of excellent optically active phosphines. A rhodium complex (Japanese Patent Application Laid-Open (JP-A) No. 55-61,973) having BINAP as a ligand and a ruthenium complex (JP-A No. 61-6,390) having BINAP as a ligand have already been reported. Further, a rhodium complex (JP-A No. 60-199, 898) having 2,2'-bis[di(p-tolyl)phosphino]-1,1'-binaphthyl (hereinafter referred to as p-TolBINAP) as a ligand and a ruthenium complex (JP-A No. 61-63,690) having the same ligand have been each reported to provide an excellent effect in an asymmetric hydrogenation reaction and in an asymmetric isomerization reaction. Furthermore, according to JP-A No. 3-255,090, a ruthenium complex of 2,2'-bis[di(3,5-dialkylphenyl)phosphino]-1,1'-binaphthyl provides an excellent effect in the asymmetric hydrogenation reaction of β-ketoesters.

However, the above-described technologies still have room for improvement for the purpose of obtaining better results in some reactions or substrates of reaction.

SUMMARY OF THE INVENTION

Accordingly, an object of the present invention is to provide a novel optically active diphosphine compound.

Another object of the present invention is to provide a novel transition metal complex which is available as a catalyst superior in such characteristics as selectivity (chemoselectivity and enantioselectivity) and catalytic activity in asymmetric synthesis reactions and a novel catalyst effective particularly in asymmetric hydrogenation reactions.

Especially, a transition metal complex of 2,2'-diphenylphosphino-5,5'-dichloro-4,4',6,6'-tetramethyl-1,1'-biphenyl (hereinafter sometimes referred to as CM-BIPHEMP) is effective in asymmetric hydrogenation reactions.

A further object of the present invention is to provide a method for making an optically active substance by the asymmetric hydrogenation reaction of hydroxyacetone in the presence of the above-mentioned transition metal complex exhibiting an excellent catalytic activity and enantioselectivity.

PREFERRED EMBODIMENTS OF THE INVENTION

The details of the present invention are given below. The optically active diphosphine compound according to the present invention is represented by the following formula:

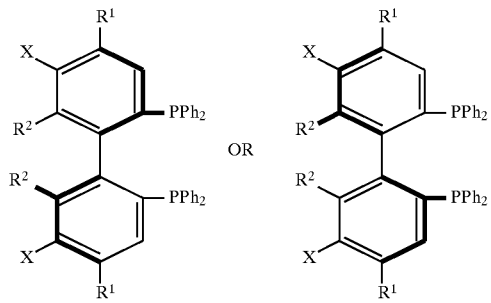

where Ph is a phenyl group, X is a chlorine or bromine atom, and $R^1$ and $R^2$ are each an alkyl group having 1 to 3 carbon atoms.

Examples of the alkyl group include methyl, ethyl, propyl and isopropyl groups.

In order to avoid unnecessary complexity, the description of the present invention centers on the example where the optically active compound is a compound represented by the formula(11) given below, but the present invention is not limited to this example.

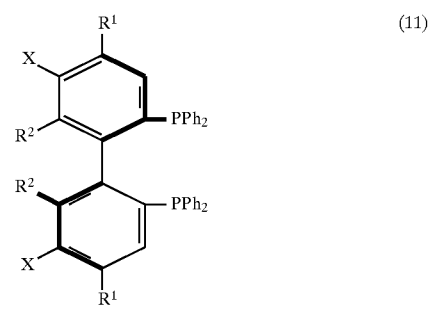

(11)

where Ph and X are the same as defined above.

Among the above-defined compounds, a preferable compound is represented by the following formula:

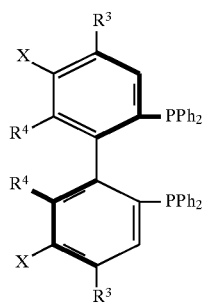
(1-1)

where Ph and X are the same as defined above and $R^3$ and $R^4$ are each a methyl or ethyl group.

A more preferable compound is represented by the following formula:

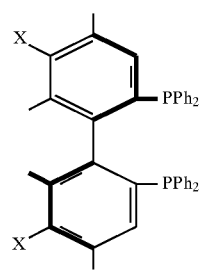
(1-2)

where Ph and X are the same as those in the preceding formula.

The most preferable compound is represented by the following formula:

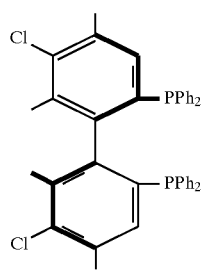
(1-3)

where Ph is the same as that in the preceding formula.

The compound according to the present invention can be prepared by carrying out a two-step reaction comprising (A) a step of preparing a monophosphinylmonotriflate from an optically active ditriflate as a starting material represented by the following formula(13):

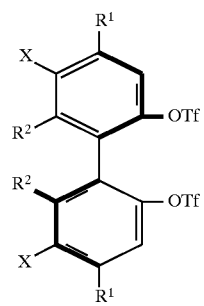
(13)

and partially reducing the thus prepared compound into an optically active monophosphinomonotriflate derivative represented by the following formula(15):

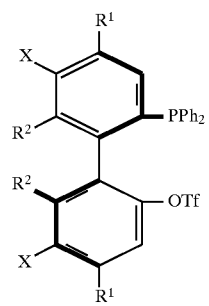
(15)

and (B) a step of preparing an optically active diphosphine oxide from the derivative of the preceding step and reducing the obtained diphosphine oxide.

The compound of formula(13) is obtained from a compound of the following formula(12) by the process known previously.

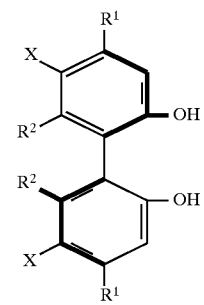
(12)

where Ph and X are the same as defined above.

The compound of the formula(13) and diphenylphosphine oxide are reactd to produce the compound of the following formula(14)

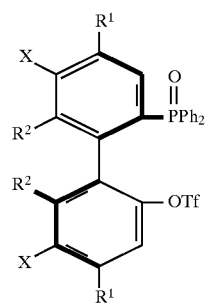
(14)

The compound of formula(14) is reduced to give the compound of the following formula(15)(The step A),

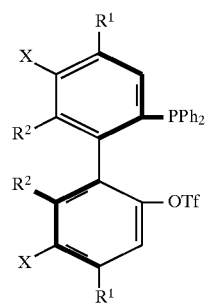
(15)

The compound of the formula(15) and diphenylphosphine oxide are reacted to produce the compound of the following formula(16).

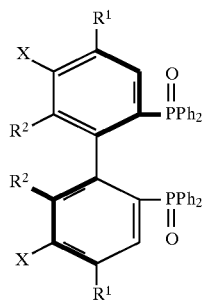

(16)

The compound of the formula(16) is reduced to give the compound according to the present invention(The step B).

In these reactions, a base and transition metal catalyst are preferably added in the reaction mixture. The preferred base includes 1,4-diazabicyclo[2,2,2]octane, diazabicycloundecene, tetramethylethylenediamine, dimethylaniline, 1,4-dimethylpiperazine, 1-methylpiperidine, 1-methylpyrrolidine, quinuclidine, 1-methylmorpholine, triethylamine, diisopropylethylamine, 1-methyl-2,2,6,6-tetramethylpiperidine. The preferred transition metal catalyst includes Rd compounds or Ni compounds.

The compound of the following formula(A) is also prepared from the compound of the following formula (B) by the same process described above.

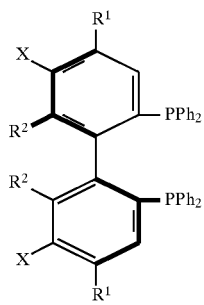

(A)

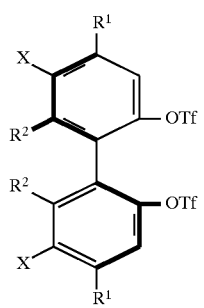

(B)

The method for making the compound according to the present invention is explained more concretely by way of a particularly preferred compound represented by the formula (1–3):

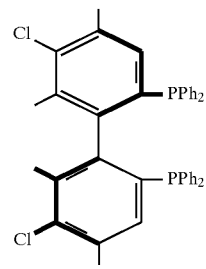

(1-3)

The compound of the formula (1-3) is prepared preferably by the method according to the following Pathway 1.

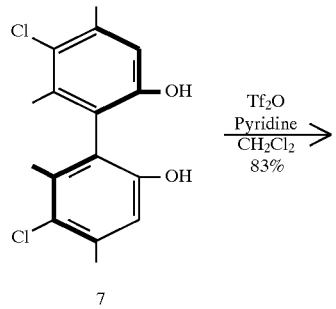

7

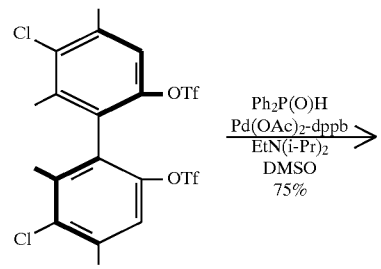

5

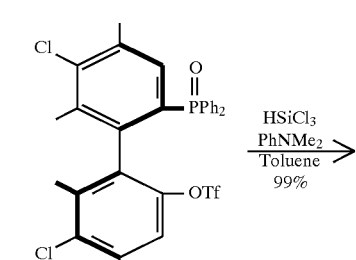

4

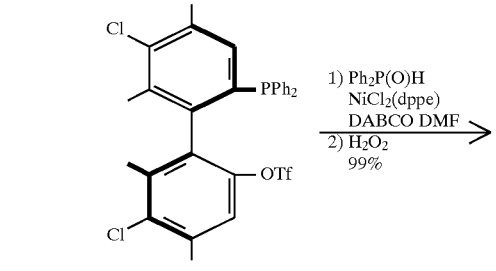

3

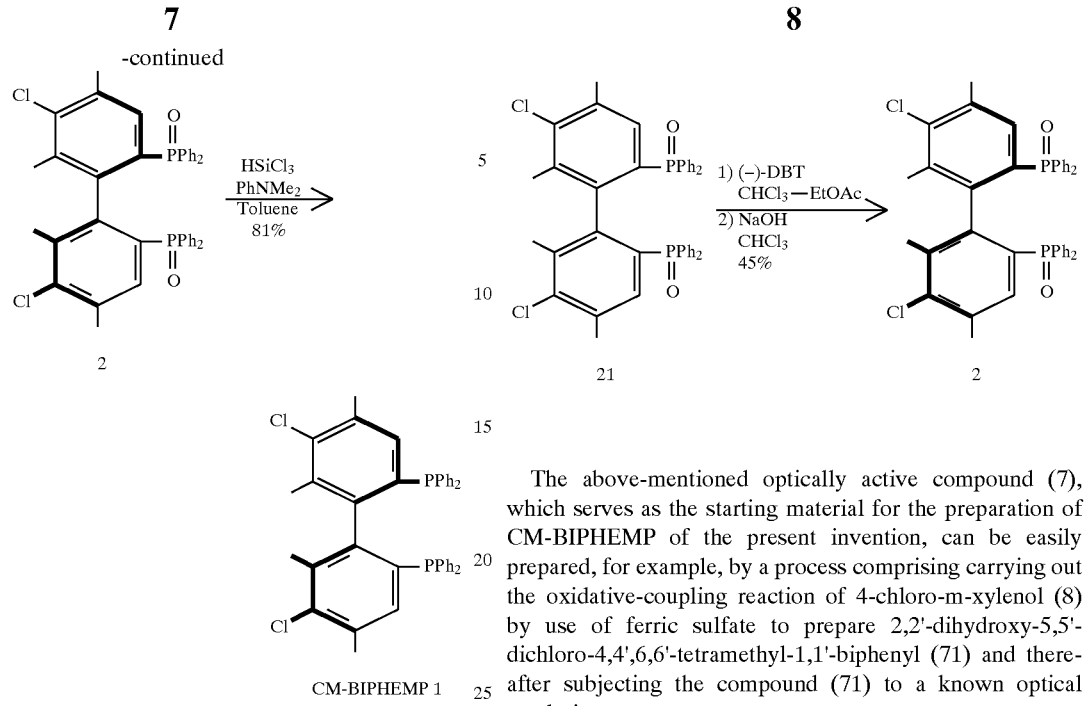

According to this pathway, an optically active compound (7) is reacted with anhydrous triflate (Tf₂O) in the presence of pyridine to prepare a ditriflate (5), which is reacted with diphenylphosphine oxide in the presence of palladium acetate, 1,4-bis(diphenylphosphino)butane (hereinafter sometimes referred to as dppb) and N,N-diisopropylethylamine to prepare a monophosphinyl compound (4).

Then, the first step is established by reducing the phosphinyl moiety of the compound (4) by use of trichlorosilane in the presence of N,N-dimethylaniline to obtain a compound (3).

The compound (3) is then reacted with diphenylphosphine oxide in the presence of a catalytic amount of a nickel/phosphine complex {Ni(dppe) Cl₂} (where dppe means 1,2-bis(diphenylphosphino)ethane) and 1,4-diazabicyclo[2,2,2]octane (hereinafter sometimes referred to as DABCO) and the resulting product is treated with a hydrogen peroxide aqueous solution to obtain a diphosphine oxide compound (2).

The compound of the formula(1-3), namely CM-BIPHEMP, can be prepared at a high yield by reducing the compound (2) by use of trichlorosilane in the presence of N,N-dimethylaniline.

Alternately, the compund, namely CM-BIPHEMP, can be prepared according to a method given below.

The procedure indicated in the above-described Pathway 1 is repeated using the same reagents except that racemic 2,2'-dihydroxy-5,5'-dichloro-4,4',6,6'-tetramethyl-1,1'-biphenyl (71) is used in place of the optically active compound (7) to prepare a racemic compound (21).

The obtained racemic compound (21) is reacted with optically active O,O'-dibenzoyl tartaric acid and the resulting product is optically resolved by use of a chloroform/ethyl acetate solvent mixture to obtain an optically active substance, which is hydrolyzed and thereafter reduced to obtain the CM-BIPHEMP as a final product (see Pathway 2).

The above-mentioned optically active compound (7), which serves as the starting material for the preparation of CM-BIPHEMP of the present invention, can be easily prepared, for example, by a process comprising carrying out the oxidative-coupling reaction of 4-chloro-m-xylenol (8) by use of ferric sulfate to prepare 2,2'-dihydroxy-5,5'-dichloro-4,4',6,6'-tetramethyl-1,1'-biphenyl (71) and thereafter subjecting the compound (71) to a known optical resolution treatment.

A preferred example of the optical resolution can be illustrated by a process comprising reacting the compound (71) with (1R, 2R)-diaminocyclohexane, optically resolving the resulting product in toluene and hydrolyzing the obtained optically active substance to form the compound (7) as a desired product (see Pathway 3).

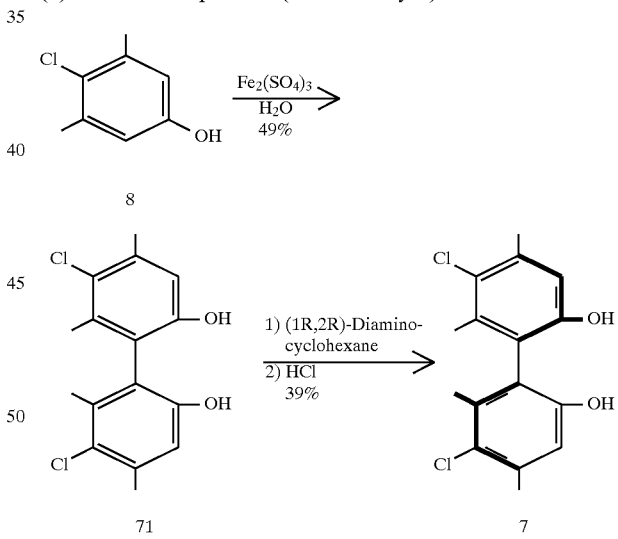

Another example of the method for obtaining the desired compound (7) can be illustrated by a process comprising transforming, in the presence of phosphorus oxychloride and (S)-(−)-1-phenylethylamine, 2,2'-dihydroxy-5,5'-dichloro-4,4',6,6'-tetramethyl-1,1'-biphenyl (71) into a phosphoric acid amide (diastereomer) optically resolving the phosphoric acid amide and hydrolyzing the resulting optically active substance (6) by means of sodium hydroxide (see Pathway 4).

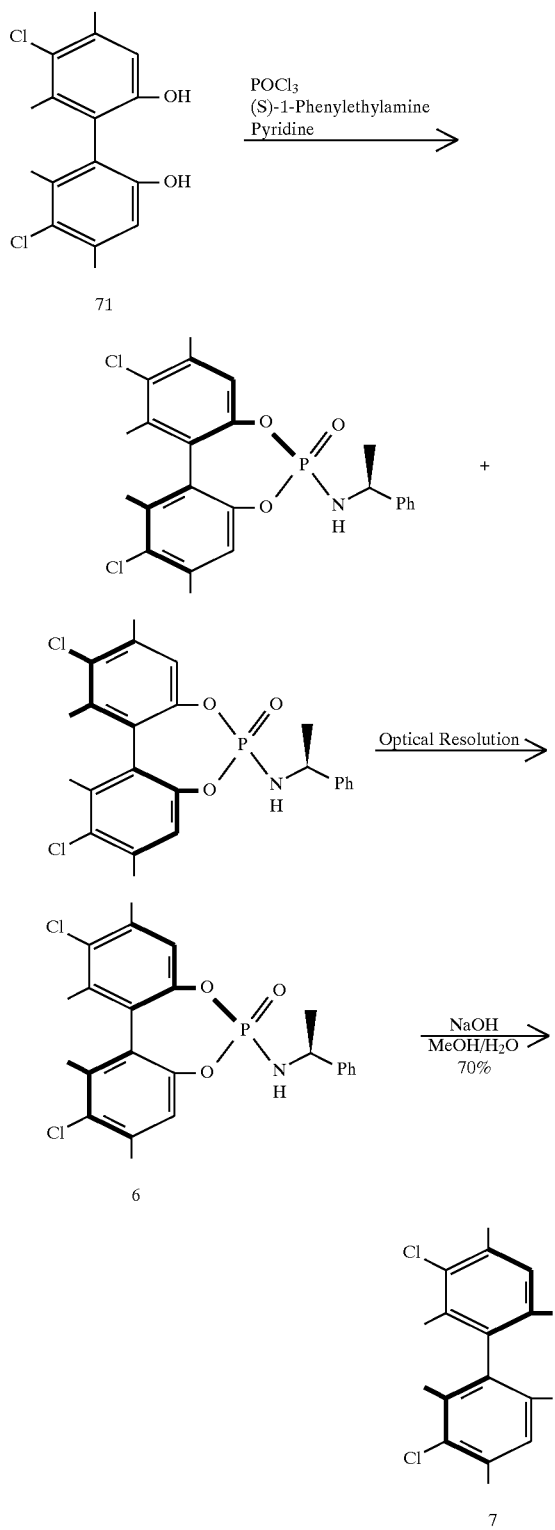

CM-BIPHEMP obtained in the above-described manner is reacted with a transition metal compound to obtain a complex, in which the CM-BIPHEMP is a ligand combined with the transition metal. This complex is particular useful as a catalyst for an asymmetric hydrogenation reaction.

This complex is represented, for example, by formula (9) or (91) indicated below:

$$MmLnXpAq \qquad (9)$$

where M stands for a transition metal and L stands for the diphosphine compound according to the present invention so that:

X is Cl, Br or I; m, n and p are each 1, and q is 0, if M is Rh;

m and n are each 1, p is 2, and q is 0, if M is Ru and X is acetoxy;

m and n are each 2, p is 4, q is 1, and A is triethylamine, if M is Ru and X is Cl;

m and n are each 1, p is 2, and q is 0, if M is Ru and X is a π-methallyl group;

X is Cl, Br or I, m, n and p are each 1, and q is 0, if 0 is Ir;

m and n are each 1, p is 2, and q is 0, if M is Pd and X is Cl;

m, n and p are each 1 and q is 0, if M is Pd and X is a π-allyl group; and

X is Cl, Br or I, m and n are each 1, p is 2, and q is 0, if M is Ni.

$$[MmLnXpAq]Dr \qquad (91)$$

where M stands for a transition metal and L stands for the diphosphine compound according to the present invention so that:

X is cod or nbd, D is $BF_4$, $ClO_4$, $PF_6$ or $BPh_4$, m, n, p and r are each 1, and q is 0, if M is Rh;

X is Cl, Br or I, A is benzene or p-cymene, D is Cl, Br or I, and m, n, p, q and r are each 1, if M is Ru;

D is $BF_4$, $ClO_4$, $PF_6$ or $BPh_4$, m and n are each 1, p and q are each 0, and r is 2, if M is Ru;

X is cod or nbd, D is $BF_4$, $ClO_4$, $PF_6$ or $BPh_4$, m, n, p and r are each 1, and q is 0, if M is Ir; and D is $BF_4$, $ClO_4$, $PF_6$ or $BPh_4$, m, n and r are each 1, and p and q are each 0, if M is Pd; wherein Ph stands for a phenyl group, cod stands for 1,5-cyclooctadiene and nbd stands for norbornadiene.

Preferred transition metal complexes and methods for making such complexes are described below.

A ruthenium complex can be prepared, for example, by heating $[Ru(cod)Cl_2]n$ and CM-BIPHEMP at reflux by use of toluene as a solvent in the presence of triethylamine as described in the literature (T. Ikariya, Y. Ishii, H. kawano, T. Arai, M. Saburi, and S. Akutagawa, J. Chem. Soc., Chem. Commun., 922 (1985)). Further a ruthenium complex can be prepared, for example, by heating $[Ru(p\text{-cymene})I_2]_2$ and CM-BIPHEMP with stirring in a methylene chloride/ethanol mixture in accordance with the method described in the literature (K. Mashima, K. Kusano, T. Ohta, R. Noyori, H. Takaya, J. Chem. Soc., Chem. Commun., 1208 (1989))

Preferred ruthenium complexes are shown in Table 1.

TABLE 1

$Ru(OAc)_2(L)$, $Ru_2Cl_4(L)_2NEt_3$,
[RuCl(benzene)(L)]Cl, [RuBr(benzene)(L)]Br, [RuI(benzene)(L)]I,
[RuCl(p-cymene)(L)]Cl, [RuBr(p-cymene)(L)]Br, [RuI(p-cymene)(L)]I,
$[Ru(L)](BF_4)_2$, $[Ru(L)](ClO_4)_2$, $[Ru(L)](PF_6)_2$, $[Ru(L)](BPh_4)_2$ Specifically, a rhodium complex can be prepared, for example, by reacting bis(1,5-cyclooctadiene)rhodium(I) tetrafluoroborate with CM-BIPHEMP in accordance with the method described in "Experimental Chemistry, 4th edition" Vol.18, Organometallic Complexes, pp.339–344, Ed. Chemical Society of Japan, 1991, Maruzen.

Preferred rhodium complexes are shown in Table 2.

TABLE 2

Rh(L)Cl, Rh(L)Br, Rh(L)I,
[Rh(cod)(L)]BF$_4$, [Rh(cod)(L)]ClO$_4$,
[Rh(cod)(L)]PF$_6$, [Rh(cod)(L)]BPh$_4$,
[Rh(nbd)(L)]BF$_4$, [Rh(nbd)(L)]ClO$_4$,
[Rh(nbd)(L)]PF$_6$, [Rh(nbd)(L)]BPh$_4$ An iridium complex can be easily prepared, for example, by reacting CM-BIPHEMP with [Ir(cod) (CH$_3$CN)$_2$]BF$_4$ with stirring in tetrahydrofuran in accordance with the method described in the literature (K. Mashima, T. Akutagawa, X. Zhang, H. Takaya, T. Taketomi, H. Kumobayashi, S. Akutagawa, J. Organomet., Chem., 1992, 428, 213).

Preferred iridium complexes are shown in Table 3.

TABLE 3

Ir(L)Cl, Ir(L)Br, Ir(L)I,
[Ir(cod)(L)]BF$_4$, [Ir(cod)(L)]ClO$_4$,
[Ir(cod)(L)]PF$_6$, [Ir(cod)(L)]BPh$_4$,
[Ir(nbd)(L)]BF$_4$, [Ir(nbd)(L)]ClO$_4$,
[Ir(nbd)(L)]PF$_6$, [Ir(nbd)(L)]BPh$_4$ A palladium complex can be prepared, for example, by reacting CM-BIPHEMP with π-allylpalladium chloride in accordance with the method described in a literature (Y. Uozumi and T. Hayashi, J. Am., Chem. Soc., 1991, 113, 9887).

Preferred palladium complexes are shown in Table 4.

TABLE 4

PdCl$_2$(L), (π-ally)Pd(L), [(Pd(L)]BF$_4$,
[(Pd(L)]ClO$_4$, [(Pd(L)]PF$_6$, [(Pd(L)]BPh$_4$ A nickel complex can be prepared, for example, by dissolving CM-BIPHEMP and nickel chloride in an isopropanol/ethanol mixture and heating the solution with stirring in accordance with the method described in "Experimental Chemistry, 4th edition" Vol.18, Organometallic Complexes, pp.376, Ed. Chemical Society of Japan, 1991, Maruzen.

Preferred examples of nickel complexes are NiCl$_2$(L), NiBr$_2$(L) and NiI$_2$(L).

The transition metal complexes prepared in the above described ways can be used as a catalyst for an asymmetric hydrogenation reaction. Although these transition metal complexes are capable of giving rise to an asymmetric hydrogenation reaction of many substances, a complex catalyst using ruthenium exhibits a markedly high activity in the asymmetric hydrogenation reaction of acetol. The asymmetric hydrogenation reaction is effected in a usual way and is not limited.

According to the present invention, many substrates undergo an asymmetric hydrogenation reaction, but acetol is the most preferred substrate for the asymmetric hydrogenation reaction.

In this case, a preferred amount of the ruthenium complex to be used is in the range of 1/10000 to 1/1000 mol based on the amount of the acetol in respect of the rapidity of the asymmetric hydrogenation reaction, chemical purity and optical purity of the asymmetric hydrogenation reaction product.

For the asymmetric hydrogenation reaction to provide desirable results, preferred conditions lie in temperatures ranging from room temperature to about 100° C., periods of reaction time ranging from 30 minutes to 72 hours and hydrogen pressures ranging from 5 to 50 atm.

The novel compound CM-BIPHEMP according to the present invention can be used as a ligand of transition metal complexes. The transition metal complex, which has CM-BIPHEMP as a ligand, is useful as a catalyst for the asymmetric hydrogenation reaction. A CM-BIPHEMP complex containing ruthenium in particular as the transition metal provides a higher enantioselectivity than a ruthenium complex of BINAP, p-TolBINAP or the like in the asymmetric hydrogenation reaction of hydroxyacetone, and is therefore highly useful in industry.

EXAMPLES

In order that those skilled in the art will be better able to practice the present invention, the following examples are given by way of illustration and not by way of limitation. The measurements in the examples were conducted by the use of the following apparatus.

Nuclear magnetic resonance:1H NMR Bruker AM400 (400 MHz) 31P NMR Bruker AM400 (162 MHz)

Melting point: Yanaco MP-500D

Optical rotation: Nihon Bunkoh Co., Ltd. DIP-4

Gas chromatography (GLC): Hewlett Packard 5890-II

High-performance liquid chromatography(HPLC): Shimadzu corporation LC10AT & SPD10A Mass spectrometry (MASS): Hitachi Ltd. M-80B Reference Example 1

Synthesis of 2,2'-dihydroxy-5,5'-dichloro-4,4',6,6'-tetramethyl-1,1'-biphenyl

A mixture of 4-chloro-m-xylenol (20.17 g, 0.125 mol), Fe$_2$(SO$_4$)$_3$ .nH$_2$O (183.6 g, 0.275 mol) and water (1.0 L) was heated at reflux for 48 hours. The reaction mixture was cooled down to room temperature and was filtered under suction. The insoluble product was dissolved in ethyl acetate (100 ml) and the solution was washed with water and a saturated sodium chloride aqueous solution in that order. After the solution was dried by means of anhydrous sodium sulfate, the solvent was distilled off at a reduced pressure to give a crude reaction product (18.55 g). The crude reaction product was recrystallized from a solvent mixture (toluene: 50 ml and acetone: 10 ml) to obtain 3.42 g of the captioned compound. The mother liquor was purified by means of silica gel column chromatography (hexane/ethyl acetate: 9/1 to 4/1 by volume) to obtain 6.06 g of the captioned compound. The total amount of the reaction product was 9.48 g (yield: 49%).

mp: 235.8–236.4° C.

$^1$H-NMR(CDCl$_3$) 66.84(2H,s), 4.62(2H,s), 2.40(6H,s), 2.04(6H,s)

Mass spectrum m/z 309[(M-H)+]

Reference Example 2

Optical resolution of 2,2'-dihydroxy-5,5'-dichloro-4,4',6,6'-tetramethyl-1,1'-biphenyl A mixture of 2,2'-dihydroxy-5,5'-dichloro-4,4',6,6'-tetramethyl-1,1'-biphenyl (20.00 g, 64.3 mmol), (1R,2R)-diaminocyclohexane (22.03 g, 192.9 mmol) and toluene (100 ml) was heated at reflux for 30 minutes. The reaction mixture was cooled down to room temperature and the resulting crystals were collected by filtration. The thus obtained crystals were recrystallized from toluene (50 ml) to give 13.7 g of crystals. The crystals were then dissolved in ethyl acetate (200 ml) and the solution was admixed with 2N hydrochloric acid (200 ml), and the resulting solution was stirred at room temperature for 1 hour. The organic layer was separated and the water layer was extracted with ethyl acetate (100 ml). These organic layers were combined into one organic solution, which was washed with water and a saturated sodium chloride aqueous solution in that order. After the solution was dried by means of anhydrous sodium sulfate, the solvent was distilled off at a reduced pressure to give 7.78 g (yield: 39.4%) of (R)-(+)-2,2'-dihydroxy-5,5'-dichloro-4,4',6,6'-tetramethyl-1,1'-biphenyl. This compound was found to be at 99%ee or more by means of liquid chromatography (column: CHIRALCEL OD-H (Daicel Chemical Ind. Ltd.); hexane/isopropanol).

[α]D24+68.8° (c=1.00, MeOH)

Reference Example 3

Optical resolution of 2,2'-dihydroxy-5,5'-dichloro-4,4',6,6'-tetramethyl-1,1'-biphenyl (a procedure different from the preceding one)

Under a nitrogen gas stream, phosphorus oxychloride (10.53 g, 68.66 mmol) was added dropwise to a solution of 2,2'-dihydroxy-5,5'-dichloro-4,4',6,6'-tetramethyl-1,1'-biphenyl (20.11 g, 64.62 mmol) and pyridine (39.12 g, 494.6 mol) in methylene chloride (80 ml) and the solution was heated at reflux for two hours. After the solution was cooled down to room temperature, a mixture of (S) -(–)-1-phenylethylamine (35 ml) and pyridine (20 ml) was added dropwise to the solution and the solution was heated at reflux for 28 hours. On completing the reaction, the solvent was distilled off at a reduced pressure and the product was dissolved in ethyl acetate (500 ml). After the organic layer was washed with 1N hydrochloric acid (200 ml), water (100 ml) and a saturated sodium chloride aqueous solution (100 ml) in that order, followed by a drying treatment by means of anhydrous sodium sulfate, the solvent was distilled off at a reduced pressure to give a product as a residue. The residue was purified by means of silica gel chromatography to give 23.25 g of a phosphoric acid amide, which was washed twice with acetonitrile (100 ml) and was recrystallized from ethyl acetate to give 6.33 g (yield: 21%) of the phosphoric acid amide. This compound was found to be at 99%ee or more by means of liquid chromatography (column: CHIRALCEL OD-H; hexane/isopropanol)

mp: 171°–181° C.;
1H-NMR(CDCl$_3$) 67.33–7.41(5H,m), 7.14(1H,s), 6.07 (1H,s), 4.65(1H,m), 3.07(1H, t, J=10.4 Hz), 2.42(3H,s), 2.23(3H,s), 2.15(3H,s), 2.11(3H,s), 1.54(3H, d, J=6.8 Hz)
31P-NMR (CDCl$_3$) 610.7(s)
Mass spectrum m/z 475(M+)
[α]D24 –83.80° (c=0.222, CHCl$_3$)

A mixture of the above-described phosphoric acid amide (3.00 g, 6.3 mmol), sodium hydroxide (1.6 g, 38.4 mmol), water (15 ml) and methanol (15 ml) was stirred overnight at room temperature. After addition of 1N hydrochloric acid (50 ml) to the solution, the product was extracted with ethyl acetate (100 ml). The organic layer, after being washed with water and a saturated sodium chloride aqueous solution, was dried by means of anhydrous sodium sulfate. Then, the solvent was distilled off at a reduced pressure to give (R)-(+)-2, 2'-dihydroxy-5,5'-dichloro-4,4',6,6'-tetramethyl-1,1'-biphenyl (1.38 g, 70% yield).

Example 1

(a) Synthesis of (R)-(–)-2,2'-bis(trifluoromethanesulfonyloxy)-5,5'-dichloro-4,4',6,6'-tetramethyl-1,1'-biphenyl Under a nitrogen gas stream, (R)-(+)-2,2'-dihydroxy-5,5'-dichloro-4,4',6,6'-tetramethyl-1,1'-biphenyl (24.00 g, 77.12 mmol) and pyridine (15.25 g, 192.80 mmol) were dissolved in methylene chloride (170 ml) and the solution was cooled down to 0° C. Then, anhydrous triflate (47.87 g, 169.67 mmol) was added dropwise to the solution and the solution was stirred overnight at room temperature. After the solvent was distilled off at a reduced pressure, the product was dissolved in diethyl ether (300 ml) and the solution was then admixed and washed with 5% hydrochloric acid (200 ml). The organic layer was washed with water and a sodium chloride aqueous solution in that order. Then, after the solution was dried by means of anhydrous magnesium sulfate, the solvent was distilled off at a reduced pressure to give 43 g of residue as a crude product. The product was dissolved in hexane (100 ml) and the solution was treated with activated charcoal and was subjected to a recrystallization treatment to give 37 g(83% yield) of the captioned product.

mp: 94°–96° C.;
1H-NMR(CDCl$_3$) δ 7.17(2H,s), 2.50(6H,s), 2.15(6H,s)
Mass spectrum m/z 574(M+)
[α]D24 –37.2° (c=0.455, CHCl$_3$)

(b) Synthesis of (R)-(+)-2-diphenylphosphinyl-2'-(trifluoromethanesulfonyloxy)-5,5'-dichloro-4,4',6,6'-tetramethyl-1,1'-biphenyl (R)-(–)-2,2'-bis(trifluoromethanesulfonyloxy)-5,5'-dichloro-4,4',6,6'-tetramethyl-1,1'-biphenyl (30 g, 52.15 mmol), diphenylphosphine oxide (purity:90%, 14.06 g, 62.58 mmol), Pd(OCOCH$_3$)$_2$ (1.17 g, 5.215 mmol), dppb (2.22 g, 5.215 mmol) and diisopropylethylamine (10.11 g, 78.22 mmol) were dissolved in dimethylsulfoxide (210 ml), and the resulting solution was stirred at 100° C. for 19 hours. 5% hydrochloric acid (300 ml) and ethyl acetate (200 ml) were added to the solution, and the solution was thereafter stirred at room temperature for 1 hour. The organic layer was separated and the water layer was extracted twice with ethyl acetate (200 ml). These organic layers were combined into one organic solution, which was washed with water (200 ml×2) and a saturated sodium chloride aqueous solution (200 ml×2) in that order. After the solution was dried by means of anhydrous magnesium sulfate, the solvent was distilled off at a reduced pressure to give a crude product (45 g), which was purified by means of silica gel column chromatography (hexane/ethyl acetate: ¾ to ¼ by volume) and washed with hexane to obtain 24.53 g of the captioned compound (75% yield) as a white solid.

mp: 165.7°–168.0° C.;
1H-NMR(CDCl$_3$) 67.35–7.55 (10H,m), 7.13(1H, d, J=13.6 Hz), 6.80(1H,s), 2.38(3H,s), 2.37(3H,s), 2.03(3H,s), 1.79(3H,s)
31P-NMR (CDCl$_3$) d 28.1(s)
Mass spectrum m/z 627(M+)
[α]D24 +25.4° (c=0.100, CHCl$_3$)

(c) Synthesis of (R)-(+)-2-diphenylphosphino-2'-(trifluoromethanesulfonyloxy)-5,5'-dichloro-4,4',6,6'-tetramethyl-1,1'-biphenyl Trichlorosilane (25.91 g, 191.26 mmol) was added to (R)-(+)-2-diphenylphosphinyl-2'-(trifluoromethanesulfonyloxy)-5,5'-dichloro-4,4',6,6'-tetramethyl-1,1'-biphenyl (24.00 g, 38.25 mmol), N,N-dimethylaniline (25.49 g, 26.7 mmol) and toluene (360 mmol) The temperature of the resulting reaction mixture was raised from 50° C. to the boiling point of the solvent over 3 hours and the reaction mixture was heated at reflux for 6 hours with stirring. Then, the reaction mixture was cooled down by the use of an ice bath and a 25% sodium hydroxide aqueous solution (200 ml) was added to the reaction mixture. The organic layer was separated and the water layer was extracted with toluene (150 ml×2). These organic layers were combined into one organic solution, which was washed with 5% hydrochloric acid (100 ml×2), water (100 ml×2) and a saturated sodium chloride aqueous solution (100 ml) in that order. After the solution was dried by means of anhydrous magnesium sulfate, the solvent was distilled off at a reduced pressure to give a residue, which was purified by means of recrystallization from hexane to obtain 20.84 g (89% yield) of the captioned compound.

mp: 126°–128° C.;
1H-NMR(CDCl$_3$) δ 7.08–7.30 (11H,m), 6.91(1H, d, J=3.3 Hz), 2.47(3H,s), 2.33(3H,s), 2.04(3H,s), 1.55(3H,s)
31P-NMR (CDCl$_3$) δ −12.4(s)
Mass spectrum m/z 611(M+)
[α]D24 +3.80° (c=0.211, CHCl$_3$)

(d) Synthesis of (R)-(+)-2,2'-diphenylphosphinyl-5,5'-dichloro-4,4',6,6'-tetramethyl-1,1'-biphenyl (R)-(+)-2-diphenylphosphino-2'-(trifluoromethanesulfonyloxy)-5,15'-dichloro-4,4',6,6'-dimetyl-1,1'-biphenyl (20.40 g, 33.36 mmol), Ni(dppe)Cl$_2$ (1.762 g, 3.34 mmol), diphenylphosphineoxide (10.76 g, 53.37 mmol) and 1,4-diazabicyclo[2,2,2]octane (7.486 g, 66.73 mmol) were dissolved in dimethylformamide (200 ml), and the resulting solution was stirred at 100° C. for 12 hours. After removal of solvent by distillation at a reduced pressure, the residue was admixed with water (150 ml) and methylene chloride (150 ml), and the resulting solution was stirred at room temperature for 1 hour. After the solution separated into layers, the water layer was extracted with methylene chloride (100 ml×2). The organic layers were combined into one organic solution, which was washed with 5% hydrochloric acid (100 ml×2) and water (100 ml×2). Then, a 10% H$_2$O$_2$ (150 ml) aqueous solution was added to the solution and the resulting solution was stirred at room temperature for 1 hour. Further, a 0.5N sodium hydroxide aqueous solution (100 ml) was added to the solution and the resulting solution was stirred at room temperature for 1 hour. After the solution separated into layers, the organic layer was washed with water (200 ml) and a saturated sodium chloride aqueous solution (200 ml) in that order. After the solution was dried by means of anhydrous magnesium sulfate, the solvent was distilled off at a reduced pressure to give 27 g of a crude product, which was purified by means of recrystallization from ethyl acetate (30 ml) to obtain 22.43 g (99% yield) of the captioned compound.

mp: 321.5°–323.0° C.;
1H-NMR(CDCl$_3$) δ 7.32–7.76 (20H,m), 6.95(2H, d, J=13.8 Hz), 2.30(6H,s); 1.34(6H,s)
31P-NMR(CDCl$_3$) δ 28.4(s)
Mass spectrum m/z 678(M+)
[α]D24 +62.60 (c=0.593, CHCl$_3$)

(e) Synthesis of (R)-(+)-CM-BIPHEMP

Trichlorosilane (1.06 g, 7.80 mmol) was added dropwise to (R)-(+)-2,2'-diphenylphosphinyl-5,5'-dichloro-4,4',6,6'-dimethyl-1,1'-biphenyl (410 mg, 0.780 mmol), dimethylaniline (1.04 g, 8.579 mmol) and toluene (15 ml), and the resulting solution was heated at reflux with stirring for 12 hours. On completing the reaction, the reaction mixture was poured into an ice-cooled 25% NaOH aqueous solution (30 ml) and the resulting mixture was stirred for 30 minutes at room temperature. After the solution separated into layers, the water layer was extracted with toluene (15 ml×2), and the organic layers were combined into a solution, which was washed with 5% hydrochloric acid (30 ml×2), water (30 ml×2) and a saturated sodium chloride aqueous solution (30 ml) in that order. After the solution was dried by means of anhydrous magnesium sulfate, the solvent was distilled off at a reduced pressure to give 430 mg of a crude product, which was purified by means of silica gel column chromatography (hexane/ethyl acetate: 5/1 by volume) and washed with hexane to obtain 410 mg of the captioned compound (81% yield) as a white solid.

mp: 219.0°–221.5° C.;
1H-NMR(CDCl3) δ 7.20–7.32 (20H, m), 6.93(2H, s), 2.32(6H, s), 1.26(6H, s)
31P-NMR(CDCl$_3$) δ −13.3(s)
Mass spectrum m/z 647(M+)
[a]D24 +58.30 (c=0.647, CHCl$_3$)

Reference Example 4
Optical resolution of 2,2'-diphenylphosphinyl-5,5'-dichloro-4,4',6,6'-tetramethyl-1,1'-biphenyl A mixture of 2,2'-diphenylphosphinyl-5,5'-dichloro-4,4',6,6'-tetramethyl-1,1'-biphenyl (19.37 g, 28.51 mmol) and chloroform (130 ml) was refluxed. To the solution was added (−)-dibenzoyl L-tartrate ester (11.26 g, 29.93 mmol) in the form of a solution in ethyl acetate (65 ml). After being stirred for 30 minutes, the reaction mixture was cooled down to room temperature and the resulting crystals (13.40 g) were collected by filtration. The thus obtained crystals were dissolved in a solvent mixture of chloroform (78 ml) and ethanol (3 ml) and the resulting solution was refluxed. Then, ethyl acetate (70 ml) was added to the solution, and the solution was left to stand at room temperature. The resulting crystals were collected by filtration. The thus obtained crystals were admixed with chloroform (100 ml) and a 2N sodium hydroxide aqueous solution (100 ml) and the resulting solution was stirred for 30 minutes. After the solution separated into layers, the organic layer was washed with a 1N sodium hydroxide aqueous solution (150 ml), water (100 ml) and a saturated sodium chloride aqueous solution (100 ml) in that order. After the solution was dried by means of anhydrous sodium sulfate, the solvent was distilled off at a reduced pressure to give 8.61 g (yield: 45%) of (+)-2,2'-diphenylphosphinyl-5,5'-dichloro-4,4',6,6'-tetramethyl-1,1'-biphenyl. This compound was found to be at 99%ee or more by means of liquid chromatography (column: CHIRALPAK OT(+) (commercially available): methanol).

Example 2
Preparation of [RuCl(benzene) ((R)-(+)-CM-BIPHEMP]Cl

A mixture, which was composed of [Ru(benzene)Cl$_2$]$_2$ (19.3 mg, 0.039 mmol), (R)-(+)-CM-BIPHEMP obtained in Example 1 (50 mg, 0.077 mmol), methylene chloride (3 ml) and ethanol (3 ml), was stirred at 50° C. for 3 hours. After removal of solvent by distillation at a reduced pressure, the product as a residue was dried in a vacuum to give the captioned product.

31P-NMR(CDCl$_3$) δ 23.7(d, J=62 Hz), 42.2(d, J=63 Hz)

Example 3
Preparation of [RuI(p-cymene) ((R)-(+)-CM-BIPHEMP]I

A mixture, which was composed of [Ru(p-cymene)I$_2$]$_2$ (37.7 mg, 0.039 mmol), (R)-(+)-CM-BIPHEMP obtained in Example 1 (50 mg, 0.077 mmol), methylene chloride (3 ml) and ethanol (3 ml), was stirred at 50° C. for 3 hours. After removal of solvent by distillation at a reduced pressure, the product as a residue was dried in a vacuum to give the captioned product.

31P-NMR(CDCl$_3$) δ 24.8(d, J=62 Hz), 42.6(d, J=59 Hz)

Example 4
Asymmetric hydrogenation of hydroxyacetone

Under a nitrogen gas stream, a mixture, which was composed of [Ru(cod)Cl$_2$]n (206 mg, 0.735 mmol), (R)-(+)-CM-BIPHEMP obtained in Example 1 (500 mg, 0.772 mmol), triethylamine (0.45 ml) and toluene (20 ml), was heated at reflux for 18 hours. After removal of solvent by distillation at a reduced pressure, the product as a residue was dried in a vacuum to give a Ru-complex (Ru$_2$Cl$_4$[(R)-(+)-CM-BIPHEMP]$_2$NEt$_3$).

The above complex (11.7 mg, 0.0067 mmol), hydroxyacetone (3.0 g, 0.041 mol) and methanol (6ml) were placed in an autoclave made of stainless steel, and the contents were stirred for 16 hours at 65° C. and hydrogen pressure of 10 atm. This reaction product was analyzed by means of gas chromatography (column: α-DEX120(Supelco Inc.)) and was found to contain 97.8% of R product and 2.2% of S product and to be at 95.6%ee. In this case, the conversion rate was 100%.

Although the present invention has been described in Conjunction with certain preferred embodiments, it is not to be limited thereto but instead includes all of the embodiments within the sprit and scope of the appended claims.

What is claimed is:

1. An optically active diphosphine compound represented by the following formula:

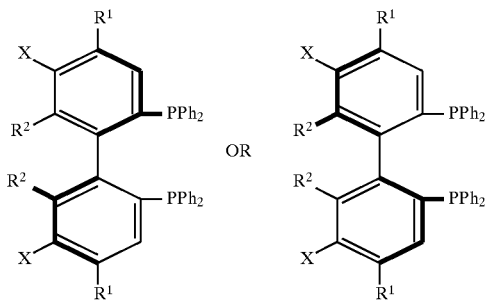

where Ph is a phenyl group, X is a chlorine or bromine atom, and $R^1$ and $R^2$ are each an alkyl group having 1 to 3 carbon atoms.

2. A method for making an optically active diphosphine compound represented by the following formula:

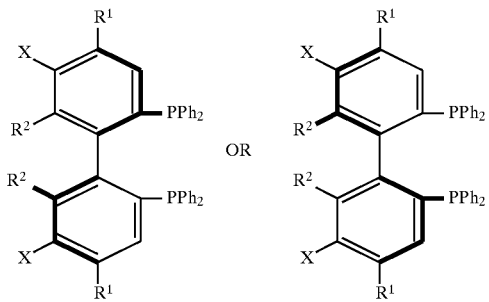

where Ph is a phenyl group, X is a chlorine or bromine atom, and $R^1$ and $R^2$ are each an alkyl group having 1 to 3 carbon atoms said method comprising (A) reacting an optically active 2,2'-dihydroxy-5,5'-dihalo-4,4',6,6'-tetraalkyl-1,1'-biphenyl ditriflate represented by the following formula:

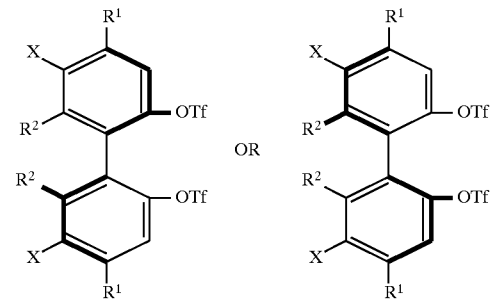

where X, $R^1$ and $R^2$ are as defined above and Tf is a trifluoromethanesulfonyl group with a diphenylphosphine oxide, to prepare an optically active monophosphinyl monotriflate derivative represented by the following formula:

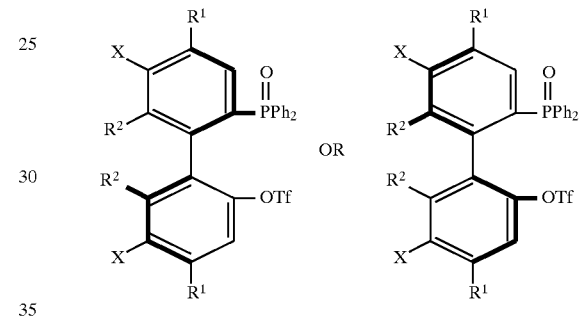

where Ph, X, $R^1$, $R^2$ and Tf are as defined above, and reducing the thus obtained compound to prepare an optically active monophosphinomonotriflate derivative represented by the following formula:

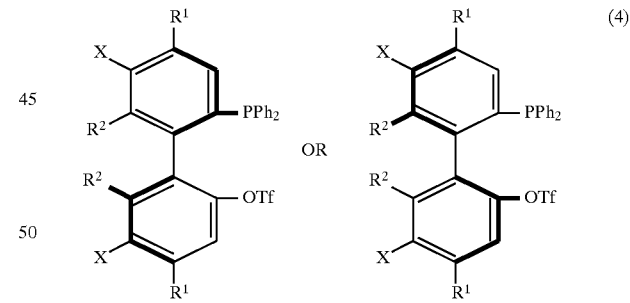

(4)

where Ph, X, $R^1$, $R^2$ and Tf are as defined above, and (B) reacting the monophosphinomonotriflate derivative of the formula (4) with a diphenylphosphine oxide to prepare an optically active diphosphine oxide compound represented by the following formula:

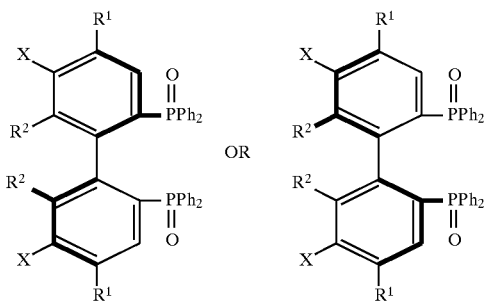

where Ph, X, $R^1$ and $R^2$ are as defined above and reducing the thus obtained compound.

3. A method for making an optically active diphosphine compound according to claim 2, wherein the reaction in (A) to prepare the monophosphinyl compound is carried out in the presence of a palladium/phosphine complex and a base and the reaction in (B) to prepare the diphosphinyl compound is carried out in the presence of a nickel/phosphine complex and a base.

4. The optically active diphosphine compound of claim 1, wherein $R^3$ and $R^4$ are each methyl or ethyl.

5. The optically active diphosphine compound of claim 4, wherein X is Cl.

* * * * *